United States Patent [19]

Kobayashi et al.

[11] Patent Number: 5,032,735
[45] Date of Patent: Jul. 16, 1991

[54] METHOD OF AND APPARATUS FOR INSPECTING PRINTED CIRCUIT BOARDS

[75] Inventors: Shigeki Kobayashi, Kyoto; Norihito Yamamoto, Shiga; Koichi Tanaka, Kyoto, all of Japan

[73] Assignee: Omron Corporation, Kyoto, Japan

[21] Appl. No.: 486,019

[22] Filed: Mar. 1, 1990

[30] Foreign Application Priority Data

Mar. 2, 1989 [JP] Japan .................................. 1-51317

[51] Int. Cl.⁵ .............................................. G01N 21/88
[52] U.S. Cl. .................................... 250/572; 356/394
[58] Field of Search ............ 250/226, 558, 572, 578.1; 356/12, 237, 376, 392, 393, 394; 358/88; 362/5, 33; 382/8

[56] References Cited

U.S. PATENT DOCUMENTS

| | | | |
|---|---|---|---|
| 4,500,203 | 2/1985 | Bieringer | 356/394 |
| 4,541,007 | 9/1985 | Nagata | 358/88 |
| 4,803,645 | 2/1989 | Ohtomo et al. | 356/376 |
| 4,876,455 | 10/1989 | Sanderson et al. | 356/394 |
| 4,894,790 | 1/1990 | Yotsuya et al. | 382/8 |
| 4,942,618 | 7/1990 | Sumi et al. | 382/8 |

OTHER PUBLICATIONS

IEE Transactions on Pattern Analysis and Machine Intelligence, vol. 10, No. 1, Jan. 1988, pp. 44-55, "Structured Highlight Inspection of Specular Surfaces", Arthur C. Sanderson et al.

Primary Examiner—David C. Nelms
Assistant Examiner—Stephone B. Allen
Attorney, Agent, or Firm—Fish & Richardson

[57] ABSTRACT

Disclosed is a method of and apparatus for inspecting a printed circuit board (PCB) for the nature of its soldered parts comprising three ring-shaped light sources which project light of different hues, the highest light source being any hue other than red, to a part mounted on a PCB at different angles and heights from above, a camera to record the reflected images, and a procedure used to check the recorded patterns to determine if the soldering is acceptable.

8 Claims, 5 Drawing Sheets

METHOD OF AND APPARATUS FOR INSPECTING PRINTED CIRCUIT BOARDS

BACKGROUND OF THE INVENTION

1. Field of the Invention

The present invention relates to methods of and apparatuses for inspecting the acceptability of soldering of parts mounted on printed circuit boards (PCBs).

2. Description of Prior Art

Originally, PCBs were visually inspected by operators for defects. Specifically, along with other questions regarding the placement of surface mounted devices on lands and their lead connections, the presence or absence, the amount, the solubility, the short, the inferior conduction, and the like of solder determine the acceptability of a PCB. But the drawbacks due to human error caused by fatigue and different standards of acceptability, not to mention the high cost of and extensive time needed for manual inspection of the increasingly small PCBs, led the industry towards automatic inspection. Unfortunately, problems dealing with cost, effectiveness, and speed of inspection still plague the art. Greatly contributing to the problems is the necessity for a reference board or a means to determine the quality of the PCBs to be inspected. Recent technology intimates that the use of reference parameters may be used to overcome these problems by determining for example the quality of a soldered portion (fillet) of a PCB.

The surface of a fillet has a shape which extends in three dimensions. In order to inspect the shape, it is essential that information on three-dimensional shapes can be detected.

FIG. 5 shows an example of an automatic inspecting apparatus capable of inspecting information on three-dimensional shapes, which projects slit light to a fillet on a PCB 2. By projecting the slit light 1, reflected light of a light cutting line 3 formed on the surface of the PCB 2 including the fillet is imaged by an imaging unit 4. Then, the imaged pattern is examined to detect the three-dimensional shape of the fillet.

However, in this inspecting method, information is only obtained on the shape of the fillet illuminated by the slit light 1. Accordingly, it is difficult to grasp the three-dimensional shapes of the other portions.

To solve this problem, there is provided a method of projecting light in a plurality of directions and at different angles of incidence to the surface of a solid bound by a curved surface to be inspected, imaging its reflective light, and detecting the orientation of the element constituting the curved surface from the respective imaged patterns. This "active sensing method" is one way to detect information on three-dimensional images. More specifically, when a light beam having a constant pattern is projected onto an object, the pattern of the reflected light beam obtained from the object is deformed corresponding to the three-dimensional shape of the object and the deformed pattern enables the estimation of the object's shape.

FIG. 6 is a diagram explaining the principle of this method, showing the positional relation between a detecting system comprising a light projecting unit 5, an imaging unit 6, and a solid bound by a curved surface which is an object to be inspected.

When a light beam 8 is projected from the light projecting unit 5, which is arranged in a given position, to the surface of a solid bound by a curved surface (i.e. a fillet) 7, the reflected light beam 9 is incident on the imaging unit 6 which is placed directly over the solid 7. Thus, the portion of the curved surface 7 illuminated by the light beam 8 is oriented at an angle of i with a horizontal reference surface 10 (i is the angle of incidence). Accordingly, when a plurality of light projecting units 5 are projected on a fillet 7, the respective angles of incidence detected by the imaging unit 6 enable the determination of the nature of the fillet 7.

Furthermore, if the light projecting unit 5 projects the light beam 8 having an incident angle ranging from $i-\Delta i$ to $i+\Delta i$, the imaging unit 6 can detect a reflected light beam 9 having a width corresponding to the range. In other words, the imaging unit 6 can detect such light as reflected from curved surfaces having an angle of $i-\Delta i$ to $i+\Delta i$ with respect to reference surface 10.

If, as in FIG. 7, the light projecting unit 5 comprises a plurality of ring shaped light sources 11, 12 and 13 having different angles of incidence to the solid bound by a curved body 7, then the elements of the curved surface having orientations corresponding to the angles of incidence of light beams 14, 15 and 16 from the sources 11, 12 and 13 can be specifically detected as described above.

The three ring-shaped light sources 11, 12, and 13 having radii of $r_m$ (m=1, 2, and 3) are horizontally arranged in positions at the heights $h_m$ (m=1, 2, and 3) from a reference surface 10. In addition, let $i_m$ (m=1, 2, and 3) be the angles of incidence of the light beams 14, 15, and 16 from the light sources 11, 12, and 13 to the solid bound by a curved surface 7. In this case, the elements of the curved surface respectively having angles of inclination of $i_m$ in the solid bound by a curved surface 7 can be detected by the imaging unit 6. The size of the element of the curved surface is sufficiently smaller than the total optical path length leading from the light sources 11, 12, and 13 and the solid 7 to the imaging unit 6. Consequently, the angle of incidence, that is, the angle of inclination of the element of the curved surface to be detected can be set by the following equation:

$$\cos i_m = h_m/(h_m^2 + r_m^2)^{1/2}$$

More specifically, the foregoing equation can be used to determine specific heights and radii for light sources such that the reflected light from each source is incident upon the imaging unit when each respective light was reflected off of a predetermined slope from the solid. Thus, the imaging unit 6 will receive incident beam 14 from the top ring-shaped light source 11 when the slope of the solid is slight or zero; when the solid 7 has a flat surface. Similarly, light source 12 will send incident beam 15 to the imaging unit 6 from where the solid 7 has a medium or gentle slope and incident beam 16 from light source 13 will only be received by the imaging unit 6 from places where the solid 7 has a steep slope.

An automatic inspecting system as described above consisting of white light sources and a monochromatic camera has been proposed (Japanese Patent Application Laid Open Publication #61-293657). However, this apparatus requires that the light sources be turned on and off instantaneously and in series in order for the imaging unit to distinguish the light received from its source. Thus, a memory for storing images obtained at different timings of projected light, an arithmetic unit for executing an arithmetic operation taking the images as the same field image, a lightning unit for causing each of the light sources to instantaneously perform a lightning operation, and the like are required.

One way to eliminate the need for this timing hardware is to distinguish the different light sources by color as in the related art submitted to the US PTO (U.S. Ser. No. 439,943). This co-pending application is not prior art, but it is related art that describes an earlier embodiment of this invention. Specifically relating to this invention is the embodiment with only one imaging unit described in FIG. 15 of U.S. Ser. No. 439,943. However, this invention is only designed to measure high-grade PCBs which are more expensive than normal PCBs because of a thin coating of solder pasted over the lands.

Referring now to FIG. 8, the light sources 24 described in U.S. Ser. No. 439,943 are from top to bottom red 28, green 29, and blue 30. First, a reference PCB 21s is placed on a conveyor 27 which is located on a y-axis table 23. This reference PCB 21s contains lands covered by copper and electrically conductive patterns formed on the epoxy resin as well as surface mounted devices. Additionally, the lands are further covered by a thin coating of solder (about 150 to 200 micrometers thick) to improve the adhesiveness between the surface mounted device's soldered lead and the land, while the patterns are covered by a rough surfaced, green colored solder resist for insulation and protection against short circuits that may be caused by stray solder. As the PCB 21s moves along the y-axis table 23, the light sources 24 project light and the reflected incident beams are imaged by an imaging unit 25, which is moving along the x-axis. At this point it should be noted that only smooth surfaces such as fillets are able to reflect distinct separate colors back to the imaging unit 25 because rough surfaces randomly diffuse the rays directed thereto, in effect mixing the colors so the incident relection appears as white light. The reference PCB 21s is used to teach the judging means 26 the size and type of parts and the like. After this first teaching has been recorded in the judging means 26, a second reference PCB 20s (not shown) without surface mounted devices is put through the imaging process to teach the judging means 26 land location information to be extracted in accordance with the data taken from the first teaching. Since the whole surface of the PCB 20s is still flat, as no surface mounted devices have yet been placed thereon, the top ringed-light source 28 will highlight the smooth, solder coated lands as red while the rough solder resist will appear as its natural color in white light which is green.

In a similar manner, the PCB to be inspected 21t is placed on the y-axis table 23, the incident beams from the light sources are imaged by the imaging unit 25 and sent to the judging means 26 for determination. Since only the smooth solder portions are highlighted by the respective colors: red for flat surfaces, green for gentle slopes, and blue for steep slopes; and the rest of the PCB is imaged as it appears in white light, the resulting image produced contains very detailed information on the nature of the soldered fillets as well as the whole PCB.

However, while U.S. Ser. No. 439,943 performs admirably on expensive high-grade PCBs with the thin coating of solder over their lands, the apparatus has problems when dealing with less expensive PCBs that have no such coating. Specifically, flat soldered portions are undistinguishable from the rough copper lands. The imaging unit views both as red. Consequently, lead connections completely lacking solder or insufficiently soldered to the lands cannot be detected.

SUMMARY OF THE INVENTION

It is one object of this invention to provide a PCB inspecting apparatus capable of inspecting all surface mounted devices on a PCB to determine if each lead is sufficiently soldered to a land.

Another object of this invention is to provide a PCB inspecting apparatus capable of determining the nature of a fillet.

It is another object of this invention to determine if the lands are in the proper locations on the PCB and that the surface mounted devices are properly mounted on the lands.

A further object of this invention is to determine if the lead connections are proper; whether the leads are properly secured to the lands or correctly inserted through the pinholes in the circuit board.

Yet another object of this invention is to provide a teaching procedure that allows an operator to adjust feature parameters regarded as defects by the PCB inspecting apparatus. This object is realized by the apparatus displaying on a CRT (Cathode Ray Tube) display unit the criteria used for a rejection. An operator, then, can determine if the supposed defect is serious enough to hinder operation of the PCB. If the operator determines that the supposed defect is not serious and will not affect operation of the PCB, then the operator can adjust the feature parameters used as criteria so the apparatus will no longer consider such a pattern as a defect. Therefore, the number of false defects can be considerably reduced as no mistake will be made twice.

Still another object of this invention is to provide an apparatus that can inspect PCBs quickly, effectively, and cost efficiently. Too often in the past, PCB inspection has been left to human operators subjected to environmental factors such as fatigue and differing standards for rejection. Thus, defective parts were bound to pass inspection unnoticed and PCBs that one person deemed acceptable were considered to be defective by another. Furthermore, prior automatic apparatuses required large memories to store reference board information. Such memories are not only expensive but also require extensive time to shift through all the details. By using feature parameters to determine defects, the PCB inspecting apparatus according to the present invention does not require such a big memory to process multitudinous information.

Another object of the invention is to reduce the size of a PCB inspecting apparatus. In prior art, PCBs to be inspected have been mounted on an xy table and then inspected by an immobile imaging means. Since the immobile imaging unit needed to view every portion of the xy table, the PCB inspecting apparatus needed space equal to four times the xy table to accommodate the table's movement along both axes. By placing the PCB to be inspected on a y-axis table and the imaging means on an x-axis table, the space needed to inspect the PCB can be reduced by ½ as only twice the area of the y-axis table is needed to accommodate the movement of the table. Furthermore, it would be impractical to place the imaging means on an xy table as the movement along both axes would induce too much vibration and hence increase the probability of imaging error, even though it would further reduce the size of the apparatus.

Another object of this invention is to provide a PCB inspecting apparatus that displays highlighted images designed for "human engineering" of all the regions of a normal PCB. In other words, to provide a highlighted color display in which human operators can easily perceive not only the different colors but also the meaning of colors. To this end, laboratory experimentation and operation has indicated that a green ring-shaped light source located at the highest height from the y-axis table, followed in height by a red ring-shaped light source, and a blue ring-shaped light source closest to the y-axis table produce the most easily distinguishable image for a human operator. Additionally, there is no problem with using green for the top light source because the lands, being rough copper, will still appear as red in the teaching process and will not be confused with the green solder resist.

Another object of this invention is to provide a PCB inspecting apparatus capable of inspecting normal PCBs. This object is accomplished by using green as the top light source. In such an embodiment, flat soldered surfaces will appear green, contrasting with the rough copper lands. Thus, an embodiment with green as the top light source is not only designed for "human engineering" but also capable of inspecting normal PCBs.

Yet another object of this invention is to provide a PCB inspecting apparatus capable of inspecting all types of PCBs. Today there are two basic genres of PCBs. Both types consist of an epoxy resin with copper coated lands as well as electrically conductive patterns formed on the epoxy resin and insulated with a solder resist. The lands are to be used as bases for mounting the leads from surface mounted devices. The first type, the high-grade type, has a thin coating (about 150-200 micrometers) of solder cream over the lands. Since solder has a very smooth surface, the different colors of light directed to the solder by PCB inspecting apparatuses are separated and the imaging means images the specific colors (i.e. red, green, and blue) that are incident on the camera. On the other hand, the other surfaces of the PCB such as: integrated circuits and other surface mounted devices, reference printing, epoxy resin, pinholes, solder resist, and the like are rough and therefore widely diffuse the colors directed thereto. As a result, the colors are mixed to be white light and the surfaces appear as their natural color on the imaging means. To avoid confusing flat and insufficiently soldered portions with the green solder resist, the apparatus described in U.S. Ser. No. 439,943 was precluded from having green as its top light source in any of its embodiments. Additionally, in consideration of "human engineering", red was preferred over blue as the top light source because the soldered portions' images thus produced were the most easily distinguishable for the operators viewing the image.

Because the process of applying the solder cream to the copper coated lands is expensive and time consuming, normal PCBs bypass the solder cream process leaving these lands uncovered. Since these copper coated lands have rough surfaces, the colors thereto directed are randomly diffused and their image appears as it would in white light. Furthermore, the color of copper in white light is nearly indistinguishable from the color of red light. Consequently, the PCB inspecting apparatus described in U.S. Ser. No. 439,943 had difficulty distinguishing flat copper lands from flat or minuscular sloped solder portions. Therefore, in this embodiment the top ring-shaped light source is blue. Since the incident light received by the imaging unit from the top light source corresponds to a flat surface being inspected, the redness of the rough copper surface is no longer a problem as the reflected image of a flat, smooth surface is blue.

In order to attain the above described objects, the present invention provides a PCB inspecting apparatus for inspecting a part mounted on a PCB for the nature of its soldered portion, which comprises a light projecting means including a plurality of ring-shaped light sources for directing light of different hues (different colors) to one part obliquely from above at different angles of incidence and with the green or blue source at the greatest height from the surface to be inspected, an imaging means located on the center line of each of the ring-shaped light sources in a position directly over the part and including a color camera for imaging reflected light of each color from the surface area of the above portion to be inspected, and a determining means to determine whether or not soldering is acceptable.

Other objects and advantages of this invention will become apparent from the following description and accompanying drawings.

BRIEF DESCRIPTION OF THE DRAWINGS

FIG. 8 is a block diagram illustrating related art.

DESCRIPTION OF THE PREFERRED EMBODIMENTS

Figure 1:
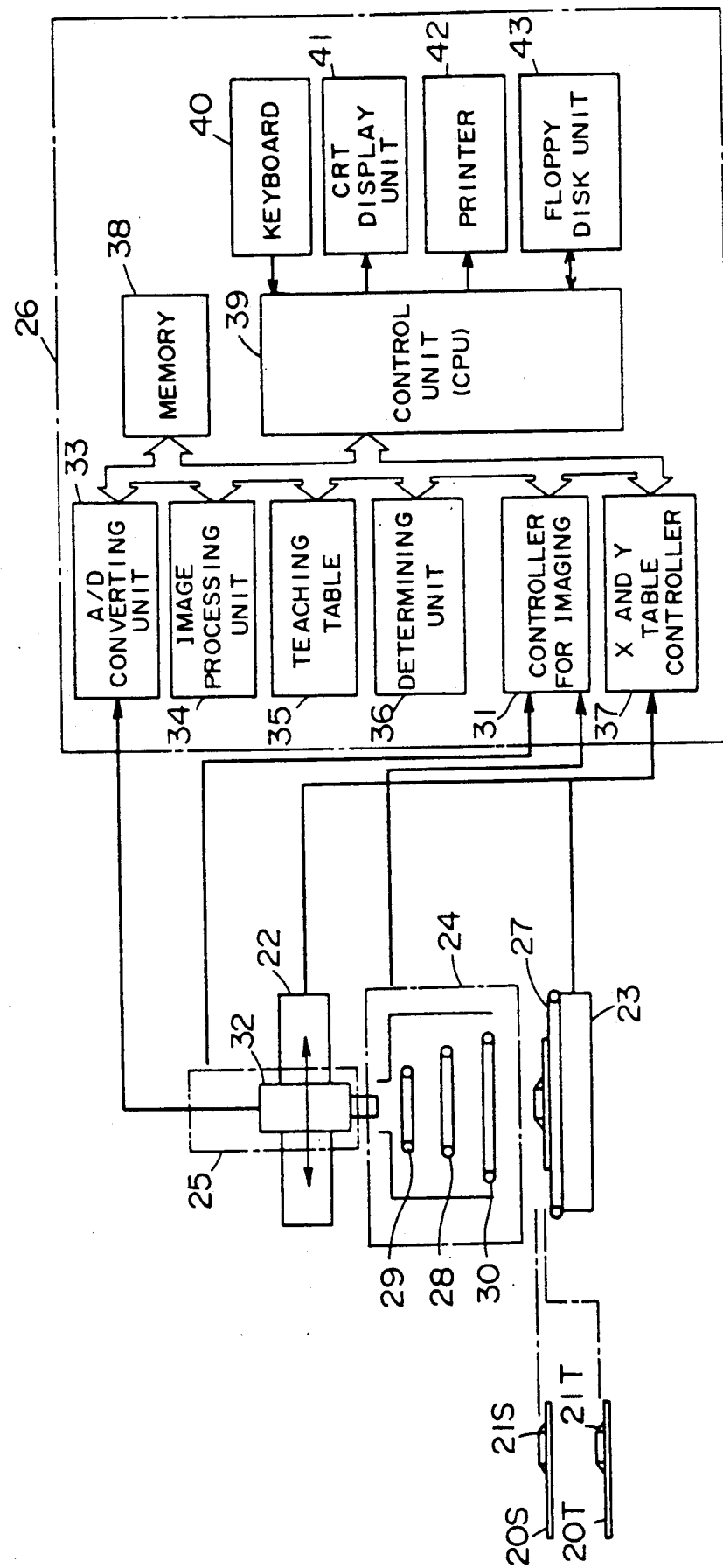
FIG. 1 is a block diagram showing one embodiment of an overall structure of a PCB inspecting apparatus of this invention.

FIG. 1 illustrates a PCB inspecting apparatus according to an embodiment of this invention. The inspection method utilized involves comparision of feature parameters of a reference PCB to the PCBs to be inspected.

First, a PCB is placed on a conveyor 27 which is located on a y-axis table 23. In the teaching process, reference PCBs 20s with reference parts 21s are studied to teach the apparatus relevant information such as: size of parts, kind of parts, printed information (labelling parts), location of parts, nature of soldering, and the like. Then PCBs 20s are studies and the apparatus extracts land information in accordance with the data taken from the first teaching. In this manner, the apparatus can determine if the parts are correctly mounted on the lands as well as their soldered condition. However, in another embodiment of this invention this second teaching process can be eliminated by incorporation into the first teaching process. In such case, only one group of reference PCBs 20s with reference parts 21s are needed to teach the apparatus. Once this information, the feature parameters, has been extracted and stored, the inspection process can begin and PCBs 20t with parts 21t are placed on the conveyor 27.

As the PCB, whether 20s, 20s with reference parts 21s, or 20t with parts 21t (hereinafter only labelled when discussing the specific PCB, i.e. PCB 20s) moves down the conveyor 27, a light projecting unit 24 projects light onto the PCB. The light projecting unit 24 comprises three ring-shaped light sources: green 29, red 28, and blue 30 having different radii and arranged in positions at different heights from the y-axis table 23. Furthermore, the smallest radius is at the greatest height from the y-axis table and, in this embodiment, is green.

When such projected light strikes the surface of the PCB, it is deflected to an imaging unit 25 located directly above the PCB and above and in the center of the ring-shaped light sources 29, 28, and 30. While the light that strikes rough surfaces such as: integrated circuits, printing, epoxy resin, through holes, copper lands, solder resist, and the like is randomly diffused and, through mixing, becomes white light; incident light striking the smooth surface of the fillets will maintain its specific color, such colored incident rays recorded by a camera 32 in an imaging unit 25, indicating the nature of the curved surface.

In the present embodiment, the light sources 29, 28, and 30 respectively have structures in which a white light source is coated with green, red, and blue transparent plates (color filters). However, the light sources are not limited to those having such structures provided that they produce light of three primary colors. For example, ring shaped flourescent lamps or neon tubing could also be used.

The incident rays reflected from the PCB are recorded by a color TV camera 32 which, together with an x-axis table 22 on which the camera 32 is placed, constitutes the imaging unit 25. By moving the PCB down the conveyor 27 in the direction of the y-axis while the camera 32 moves in the direction of the x-axis, all of the regions of the PCB are able to be detected. This movement is directed by an x and y table controller 37 which is located in a processing unit 26. The detected images are then converted to electrical signals by the imaging unit 25 and sent to an anolog/digital (A/D) converter 33 which is part of the processing unit 26.

Besides an A/D converter 33 and an x and y table controller 37, the processing unit 26 further comprises: an image processing unit 34, a teaching table 35, a determining unit 36, a controller for imaging 31, a keyboard 40, a cathode ray tube (CRT) display unit 41, a printer 42, a floppy disk unit 43, a memory 38, and a control unit (CPU) 39.

The A/D converter 33 converts the colored signals of green, red, and blue into digital signals and supplies the same to the random access memory (RAM) 38. The RAM 38 serves as a work area for the CPU 39 and sends the digital signals thereto. Subsequently, the CPU 39 directs the digital signals to the image processing unit 34 which binarizes the aforementioned signals to a color threshold to distinguish each color from the other, creating file holding data. The image processing unit 34 performs this function three times, once for each color. Then, this file holding determining data is returned to the CPU 39 and also distributed to the determining unit 36 or the teaching table 35 if the apparatus is in the teaching mode.

The teaching table 35 stores the file holding determining data when it is supplied from the CPU 39 in the teaching mode. Determining data or feature parameters are for example: width of fillet, end of lead, land location, degree of slope, type of part mounted, direction of mounting, and the like. The teaching table 35 stores the average value of each from the teaching PCBs 20s and 20s with reference parts 21s. There are many feature parameters each further broken down into conditions, in which a majority must be met to satisfy the parameter. In the inspection mode, the teaching table 35 reads out this file holding determining data according to a transfer request to supply the file holding data to the CPU 39 and the determining unit 36.

The determining unit 36 compares the file holding determining data supplied from the CPU 39 in the inspection mode with the file holding data to be inspected, which was transferred from the the image processing unit 34, to determine whether or not a soldered state is good with respect to the PCB 20t with parts 21t to be inspected. Then, the determining unit 36 outputs the results of the determination to the CPU 39.

Figure 2:
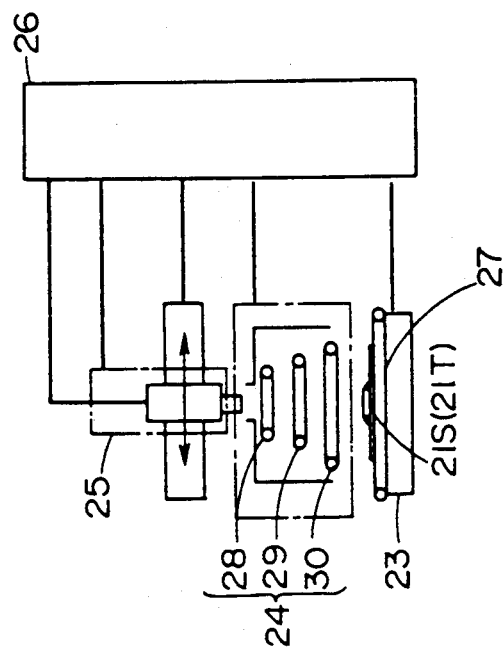
FIG. 2 illustrates soldering quality and its relation to feature parameters.

FIG. 2 illustrates the relation between soldering quality and the determining data, the feature parameters. Examples of good soldering, acceptable soldering, unacceptable soldering, and no solder are illustrated in cross-sectional views and from the view of the actual imaged pattern, which is broken down into the respective colors making up the pattern. FIG. 2 corresponds to an embodiment of this invention where the top light source is green, the middle source is red, and the bottom source is blue; hence the soldered portions 44 that are flat appear as green imaged patterns (    ), the gentle slopes are red (=), and the steep areas of the fillet are blue (////). When the condition of the soldering is unacceptably low, only a very thin layer covers the land 45 and, though it appears adequately silver (solder colored) in white light, the resultant image P is predominantly green. In cases of no solder, the redness P' is the flat but rough surfaced copper land combines with some incident green rays P' to produce a yellowish image on the CRT display unit 41. Thus, the above difference in colors enables cases of low soldering to be distinguished from cases of no soldering.

Again referring to FIG. 1, the image controller 31 and the x and y table controller 37 ensure that the whole PCB is imaged. The image controller 31 comprises, for example, an interface for connecting the CPU 39 with the light projecting unit 24 and the imaging unit 25 and controls, on command from the CPU 39, the amounts of light emitted by the respective light sources 29, 28, and 30; maintaining a balance between light output of hues of the color television camera 32 to the imaging unit 25.

The x and y table controller comprises, for example, an interface for connecting the CPU 39 to the x-axis table 22 and the y-axis table 23; controlling the tables in response to commands from the CPU 39.

The CRT display unit 41 comprises a cathode-ray tube and displays on its screen image data that is the result of the determinations of feature parameters, keyboard input data, and the like when such data is supplied from the CPU 39. The printer 42 prints out the results of the determination and the like when the same is supplied from the CPU 39. The keyboard 40 comprises various keys required for entering information on operations, data on the reference PCBs 20s and 20s with reference parts 21s, the PCB to be inspected 20t with parts 21t, and the like to be supplied to the CPU 39.

The CPU 39 includes a microprocessor and the like and controls operations in teaching and inspection through the following procedures.

Figure 3:
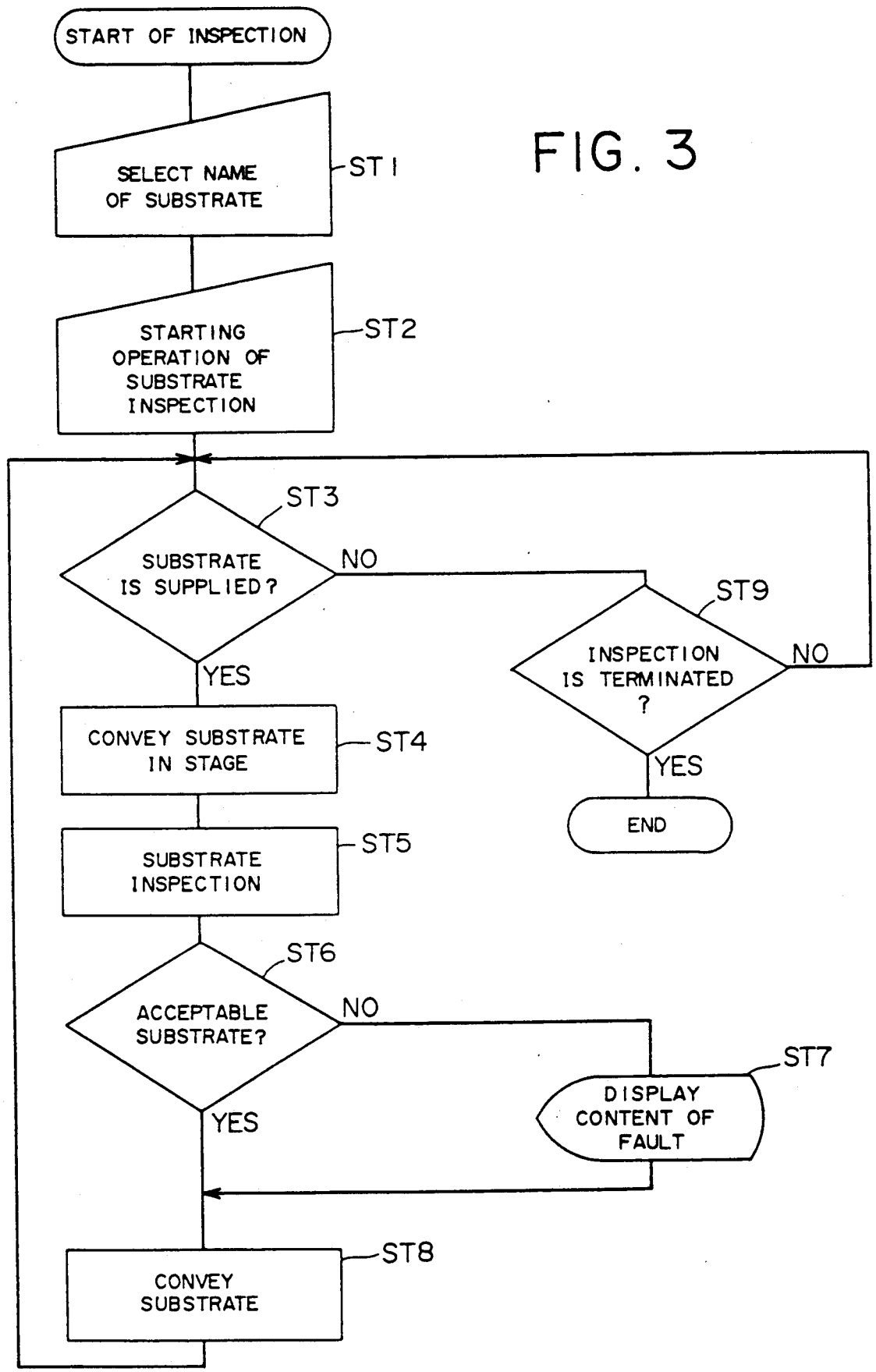
FIG. 3 is a flow chart showing the procedure for teaching processing.

Referring to FIG. 3, a flow chart for describing one embodiment of a teaching procedure, the start of teaching comprises the CPU 39 turning on the light projecting unit 24 and the imaging unit 25 to arrange the conditions for imaging and for data processing. In the first step (ST1), an operator operates the keyboard 40 to register the name and input the size of the first teaching PCB 20s with reference parts 21s. ST2 comprises starting the operation of position detecting processing whereby the operator places the first teaching PCB 20s with reference parts 21s on the y-axis table unit and depresses a start key. In ST3, inputting the reference points of the PCB, the upper right-hand and lower left-hand corner portions are imaged in the imaging unit 25 as the origin of the reference PCB 20s with reference parts 21s and then displayed on the CRT display unit 41. When the operator positions the cursor in each of the above corner portions and depresses a particular key, the coordinates of the cursor position are inputted as the coordinates of the corner portions. The CPU 39 then controls the x-axis table 22 and the y-axis table 23 on the basis of the coordinate data to place the PCB in its initial position.

Once the reference PCB 20s with reference parts 21s is in its initial position, teaching of position and type of each part occurs in ST4. Each part 21s is imaged by the imaging unit 25 and analyzed by the image processing unit 34 to determine the labels representing the part, the direction of mounting, the position on the PCB 20s, the shape, the color, the nature of the soldering, and the like to teach the type and position of mounting for each part 21s.

When this is accomplished for each part, the setting of a region to be inspected is performed in ST5. In general, a part has numerous leads around its periphery that are soldered to a land on the PCB; the area around this is the region to be inspected. The setting of the regions to be inspected comprises y-axis location exraction from the images obtained by the imaging unit 25 for each part's region of the PCB.

Once the regions to be inspected have been set, the teaching process is repeated on a teaching PCB 20s. Determinations on size and location of lands and patterns are produced by following ST1 through ST5 and in this manner the proper mounting of the parts on the lands is ensured.

At this point, the procedure for teaching a feature parameter begins. ST6 comprises the CPU 39 initializing the number (n) of teaching PCBs to 1. Then, in ST7, the starting operation of feature extract processing is accomplished by the operator placing the first PCB 20s with reference parts 21s on the y-axis table unit 23 and depressing the start key of the keyboard 40. The CPU 39 controls the x-axis table unit 22 and the y-axis table unit in response to the data obtained on the position of the parts and the regions to be inspected obtained in ST4 and ST5 in order to sequentially position the fields of view of the television camera 32 to image the PCB 20s with reference parts 21s.

Finally in ST8, the extracting processing of feature parameters is performed. The electronic color signals of the three primary colors, green, red, and blue that were obtained by the imaging unit are converted into digital data by the A/D converter 33 and stored in the RAM 38 on a real time basis. Then, the CPU 39 extracts land portions within each part's region and reads out image data of the respective hues from the RAM 38 and sends the same to the image processing unit 34. The image processing unit 34 then binarizes the color signals according to a threshold for each color, making each color distinct. In this manner, the normal soldered state with respect to green, red, and blue patterns is calculated to become the feature parameters to be used for inspecting.

When the feature parameters have been determined for each region on a PCB 20s with reference parts 21s, the CPU 39 judges, ST9, whether all reference PCBs have been scrutinized. If not, then the teaching procedure moves on to ST10 and the counter n is increased by 1. Then the procedure for teaching a feature parameter is resumed at ST7 until all PCBs have been scrutinized. Eventually the CPU's 39 judgement in ST9 will be yes and the teaching process will proceed to ST11.

In ST11, the CPU 39 generates the teaching table 35 by subjecting each of the feature parameters associated with the n reference PCBs 20s with reference parts 21s to statistical processing to calculate the average value and the standard deviation so as to obtain the average amount of features for each of the parts. Then, the CPU 39 creates a file holding determining data taking the range corresponding to the average value multiplied by a constant, thus obtaining the normal range of standard deviation to be filed in the teaching table 35. The CPU 39 then corrects any data required to terminate teaching and the apparatus is primed for inspection.

Figure 4:
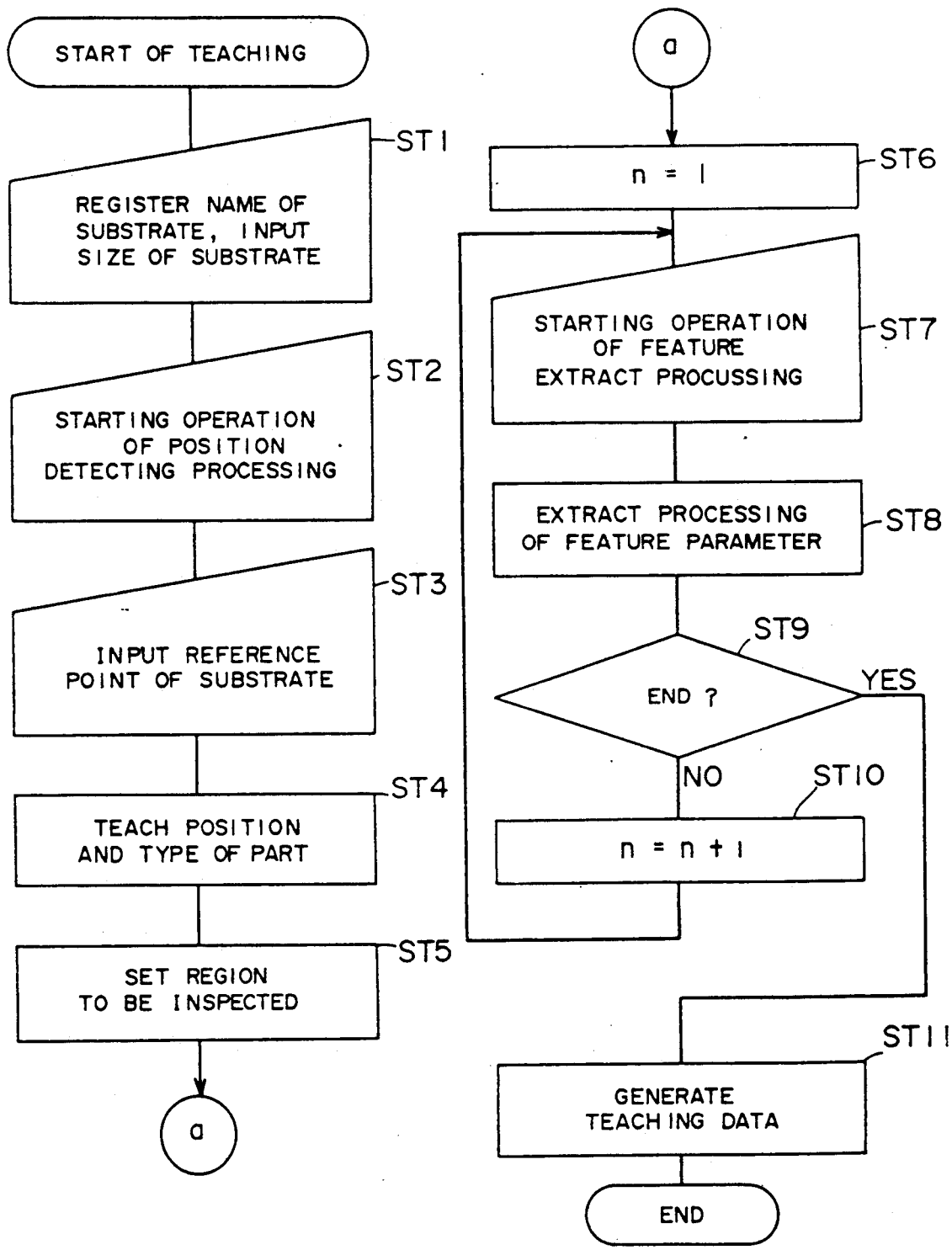
FIG. 4 is a flow chart showing the procedure for inspection processing.
Figure 6:
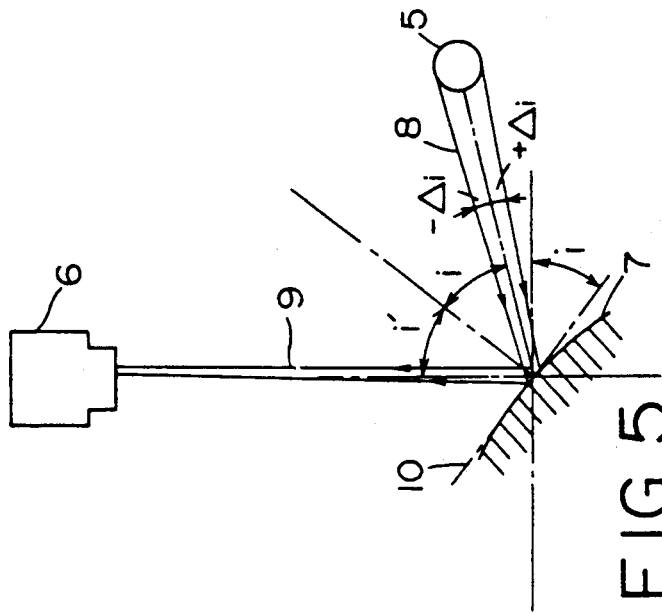
FIGS. 6 and 7 are diagrams for explaining the principle of inspection in an automatic inspecting apparatus.
Figure 5:
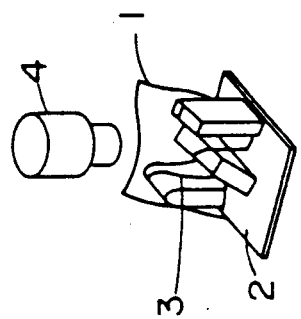
FIG. 5 illustrates the principle of a conventional automatic inspecting apparatus.
Figure 7:
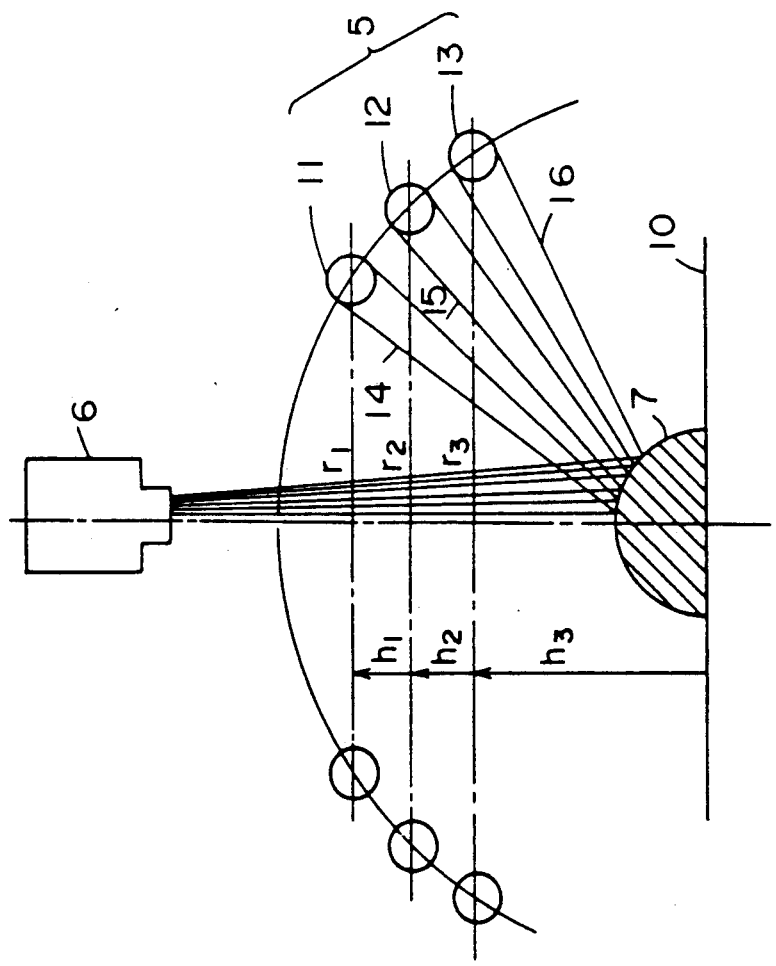

FIG. 4 illustrates a flow chart depicting an embodiment of an inspection procedure. After the start of the inspection process, the operator selects the name of the PCB to be inspected ST1 and then starts the operation of PCB inspection ST 2. Next, in ST3, the CPU 39 judges whether PCB 20t with parts 21t has been supplied to the apparatus. If yes, then the conveyor 27 is operated ST4 and the PCB 20t with parts 21t is conveyed into the y-axis table 23 and inspected ST5.

During ST5, the CPU 39 controls both the x-axis table 22 and the y-axis table 23, positions the field of view of the television camera 32 with respect to the first part 21t on the PCB 20t to be inspected to image the PCB, automatically extracts land portions in the region to be inspected, and calculates feature parameters in each of the land portions; creating file holding data to be inspected. Then, the CPU 39 transfers the above file holding data to the determining unit 36 to compare with the file holding data stored in the teaching table 35. In this manner, ST6, the determining unit 36 determines whether or not soldering is acceptable with respect to the first part 21t.

Such inspection is repeatedly made with respect to all parts 21t on the PCB 20t to be inspected. If the soldering of a part 21t is unacceptable, ST7, then the faulty part 21t and the contents of the fault (i.e. the conditions that are based on feature parameters that are in turn used to determine soldering acceptability) are displayed on the CRT display unit 41 or printed by the printer 42. Thus, the operator can see the reasons why the apparatus declared a part 21t a defect and in the case of a false defect the operator is enabled to alter the conditions used by the apparatus to make its determination. In this manner, numerous false defects can be simply avoided. If, on the other hand, the soldering is determined to be acceptable for all parts 21t, ST8, then the PCB 20t is conveyed out of the y-axis table 23. The CPU 39 then judges, ST9, if all PCBs to be inspected 20t with parts 21t have indeed been inspected. If not, then the next PCB is supplied and the procedure begins again at ST3. Once all PCBs 20t with parts 21t have been inspected, the inspection is terminated and the inspection process ends.

The above described invention comprising the light projecting unit 24 with the three ring-shaped light sources, with green 29 on top, red 28 in the middle, and blue 30 closest to the y-axis table 23 is able to inspect all normal PCBs; PCBs with copper lands. However, by changing the embodiment of the light sources, this invention can be made to inspect all genres of PCBs. Specifically, this apparatus can inspect both normal PCBs and high-grade PCBs if, in another embodiment, the blue 30 light source is on top, regardless of whether red 28 or green 29 comprise the middle or lowest ring-shaped light source. In an embodiment with blue 30 as the top light source, the flat surfaced fillets will appear as blue; easily contrasting with the reddish copper lands of a normal PCB as well as with the green solder resist that covers the patterns formed on the epoxy resin.

The above description and accompanying drawings are merely illustrative of the applications of the present invention and are not limiting. Many other embodiments falling under the spirit and scope of this invention may be devised by those skilled in the art. Accordingly, this invention is only limited by the scope of the appended claims.

What is claimed is:

1. A printed circuit board (PCB) inspecting apparatus for inspecting a part mounted on a PCB for the nature of its soldered portion, comprising:

a light projecting means including a plurality of ring-shaped light sources for directing light of different hues to said part obliquely from above at different angles of incidence;

the top light source comprising any hue other than red;

an imaging means including a color camera located in the center of the ring-shaped light sources and directly over the part for imaging reflecting light from the surface of said portion to be inspected; and a determining and processing means for detecting the nature of the soldered portion by an imaged pattern obtained by the imaging means to determine soldering acceptability.

2. The apparatus according to claim 1, wherein said light projecting means comprises three ring-shaped light sources.

3. The apparatus according to claim 2, wherein said ring-shaped light sources comprise the hues of green, red and blue.

4. The apparatus according to claim 3, wherein said ring-shaped light sources are comprised of different radii and different heights from the PCB.

5. The apparatus according to claim 4, wherein said radii are smallest at the greatest height from the PCB and largest at the least height from the PCB.

6. The apparatus according to claim 5, wherein said ring-shaped light source at the greatest height from the PCB is green.

7. The apparatus according to claim 5, wherein said ring-shaped light source at the greatest height from the PCB is blue.

8. A method for inspecting a PCB for determining if lands are in the proper locations, surface mounted devices are mounted correctly to said lands, and if leads of said surface mounted devives are correctly soldered to said lands, wherein a light projecting means projects different hues of light at a PCB, the top light source comprising any hue other than red, the incident reflection of said light on an imaging means maintains its distinct hue when incident from a smooth surface such as solder and mixes to become white light when incident from a rough surface such as epoxy resin, and a determining and processing means that compares feature parameters of said incident reflections.

* * * * *